Figure 1A:
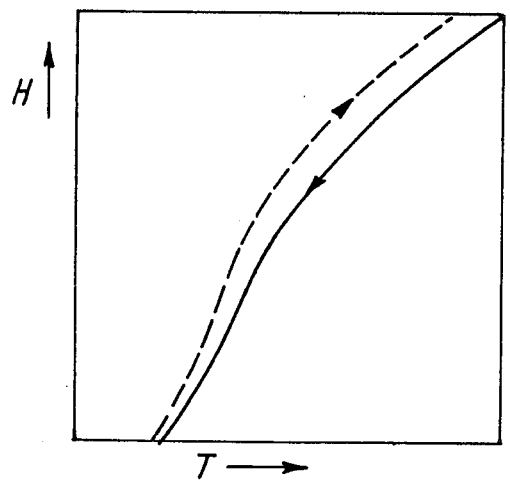

United States Patent [19]

Duckett et al.

[11] Patent Number: 4,461,634

[45] Date of Patent: Jul. 24, 1984

[54] SEPARATION OF GAS MIXTURES BY PARTIAL CONDENSATION

[75] Inventors: Melvyn Duckett, Marple; Gregory J. Ashton, Stockport; David R. Salisbury, Heywood, all of England

[73] Assignee: Petrocarbon Developments Limited, Manchester, England

[21] Appl. No.: 368,709

[22] Filed: Apr. 15, 1982

Related U.S. Application Data

[63] Continuation-in-part of Ser. No. 311,006, Oct. 13, 1981, abandoned.

[30] Foreign Application Priority Data

Oct. 16, 1980 [GB] United Kingdom ............... 8033468
Apr. 14, 1982 [GB] United Kingdom ............... 8210820

[51] Int. Cl.$^3$ ............................................. F25J 3/02
[52] U.S. Cl. ............................................. 62/11; 62/40
[58] Field of Search ............... 62/9, 11, 40, 36, 41; 203/DIG. 4, 24, 26

[56] References Cited

U.S. PATENT DOCUMENTS 3,592,015 7/1971 Streich et al. ............... 62/40
3,747,359 7/1973 Streich ............... 62/40
3,818,714 6/1974 Etzbach et al. ............... 62/11

OTHER PUBLICATIONS

F. Reif, Fundamentals of Statistical and Thermal Physics, 1965, pp. 178–184.

Primary Examiner—Frank Sever
Attorney, Agent, or Firm—Curtis, Morris & Safford

[57] ABSTRACT

In a process for the separation of a gas mixture at superatmospheric pressure by partial condensation at cryogenic temperatures and wherein the separated condensate and uncondensed vapor are passed back as returning streams in indirect countercurrent heat exchange relationship with the incoming feed mixture, the power required for providing the refrigeration and energy requirements for the separation are reduced by supplying said requirements by means of a heat pump alone or together with at least one separate refrigeration cycle and/or some Joule-Thomson expansion of the condensate, and in the heat pump a compressed multi-component gaseous medium is condensed by heat exchange with said returning streams over a first temperature range and then expanded by Joule-Thomson expansion, and the expanded condensate is evaporated by heat exchange with the feed gas mixture over a lower temperature range than said first temperature range, and recycled for recompression.

18 Claims, 7 Drawing Figures

"CROSSOVER"

"OVER REFRIGERATED"

SEPARATION OF GAS MIXTURES BY PARTIAL CONDENSATION

This is a continuation-in-part of application Ser. No. 311,006 filed Oct. 13, 1981 now abandoned.

This invention is concerned with the separation of gas mixtures into two or more streams of differing composition by partial condensation at sub-ambient temperatures. It is particularly applicable when the feed mixture is available at an elevated pressure and the products of separation are themselves required to be provided at as high a pressure as possible.

A favoured procedure is to cool the feed mixture with returning cold products until a suitable portion has been liquefied, thereupon to separate liquid and vapour phases, return the vapour as one product substantially at feed pressure, expand the liquid to a lower pressure and evaporate it in countercurrent with the entering feed stream to provide cold for the process.

If this single partial condensation is inadequate to produce the required separation, further steps are needed, which may involve partial evaporation of liquid, partial condensation of vapour and/or fractional distillation. Separation products, where not required to be provided as cold liquids, are normally returned through the heat exchange system, serving to cool the feed stream.

It all the products are to be delivered in the gaseous state at ambient temperature, the Joule-Thomson effect associated with the expansion of the liquid is often adequate to supply the required refrigeration, which is limited to overcoming cold losses to the surroundings and maintaining a suitable temperature difference between feed and products at the warm end of the heat exchange system. However, since the Joule-Thomson effect is roughly proportional to the pressure difference between compressed and expanded streams, the refrigeration requirements can be satisfied only if, with a given feed pressure, the pressure after expansion is below a certain limit. Otherwise additional refrigeration has to be provided, which may involve a work-expansion step, an external refrigeration cycle or some suitable combination requiring capital expenditure and generally some consumption of utilities.

A practical cryogenic gas separation process involving partial condensation and in which refrigeration is provided entirely by Joule-Thomson expansion of condensate, has to fulfill three conditions.

1. The overall enthalpy increase of the products returning through the heat exchange system must equal the required enthalpy decrease of the feed stream.
2. At every point in the heat exchange system the temperature of the feed stream must be higher than that of the returning streams.
3. For reasons of thermodynamic efficiency the temperature difference between feed stream and returning products should be as small as is compatible with an acceptable heat exchange surface.

These conditions can be shown on a graph, in which the enthalpy (H) of the feed stream as a function of temperature (T) is plotted as a "cooling curve" and the sum of the enthalpies of the returning streams is similarly plotted as a "combined warming curve". In a practical system the two curves must have the same overall height, the warming curve must lie entirely to the left of the cooling curve, and the horizontal distance between the two curves must be small throughout the whole temperature range, but not so small as to require an inordinately large surface for heat transfer.

Figure 1B:
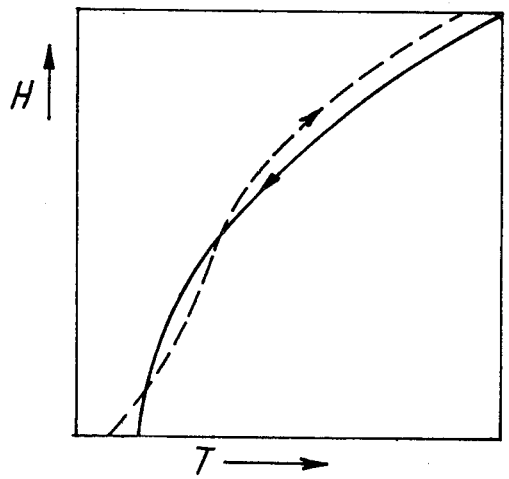
Figure 1C:
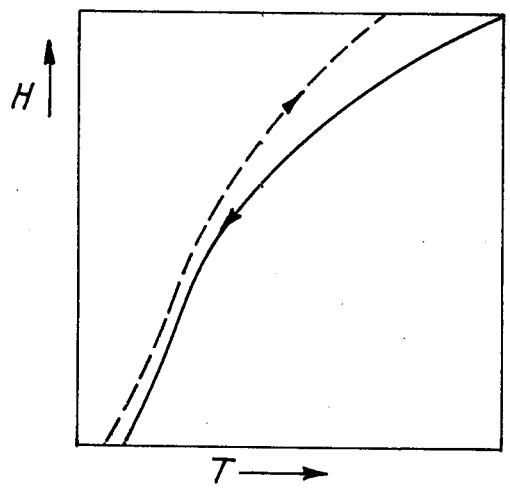
Figure 2:
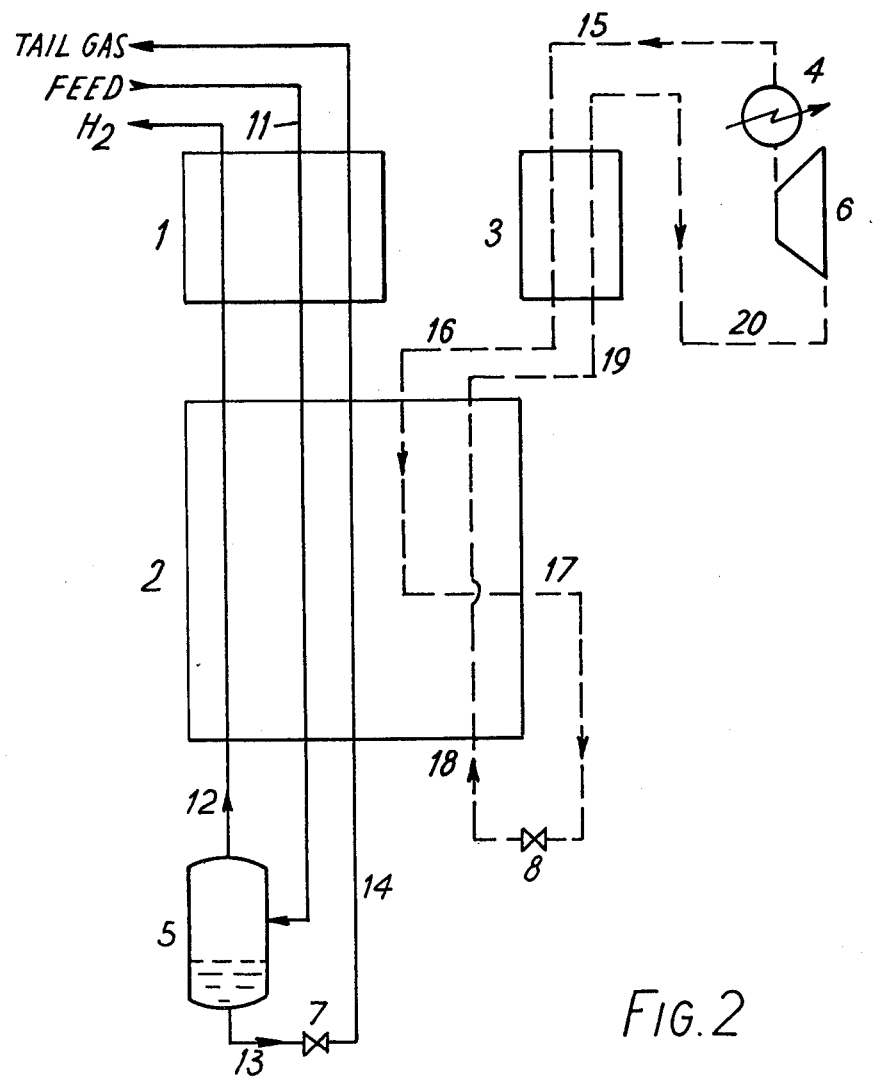
Figure 3:
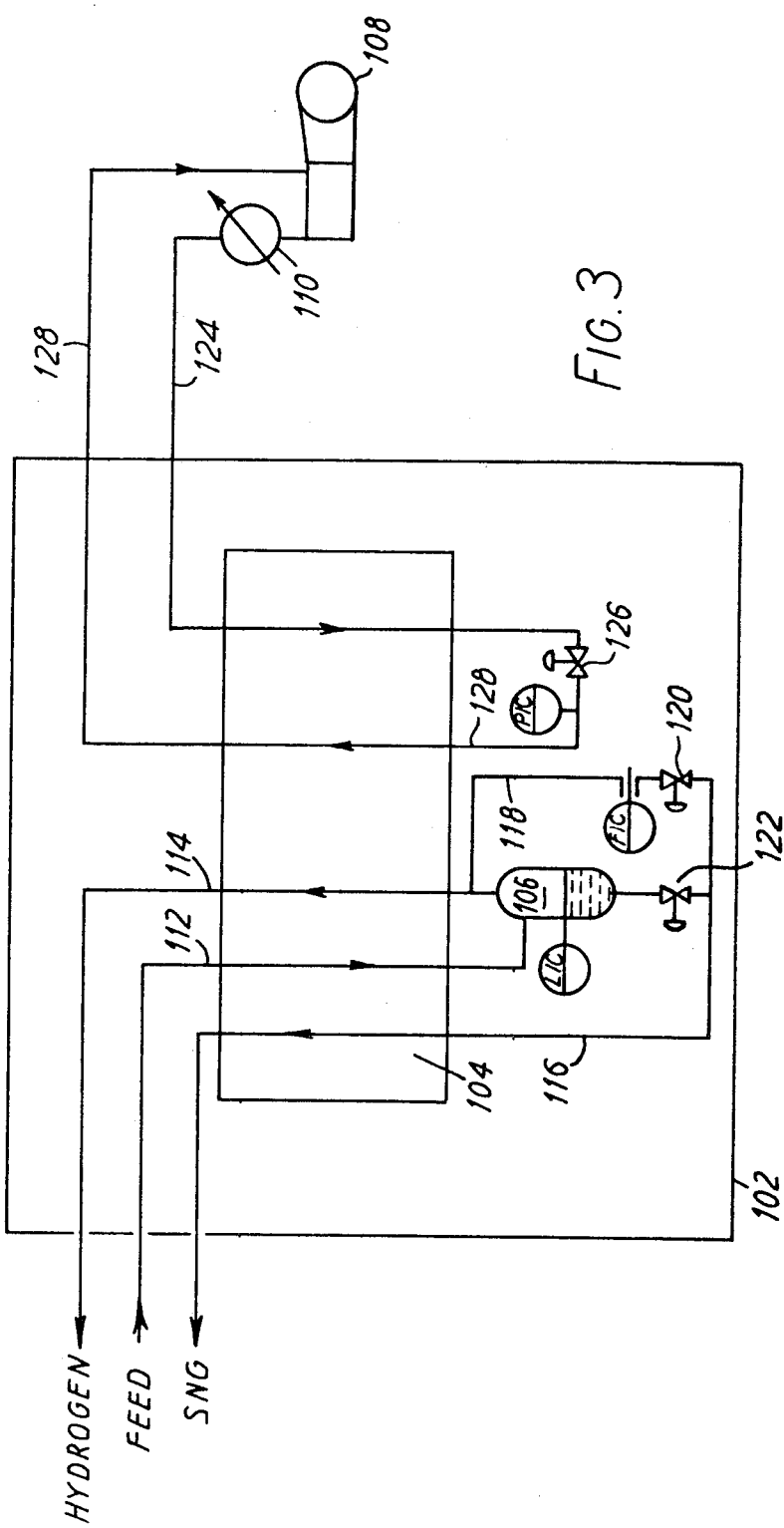
Figure 4:
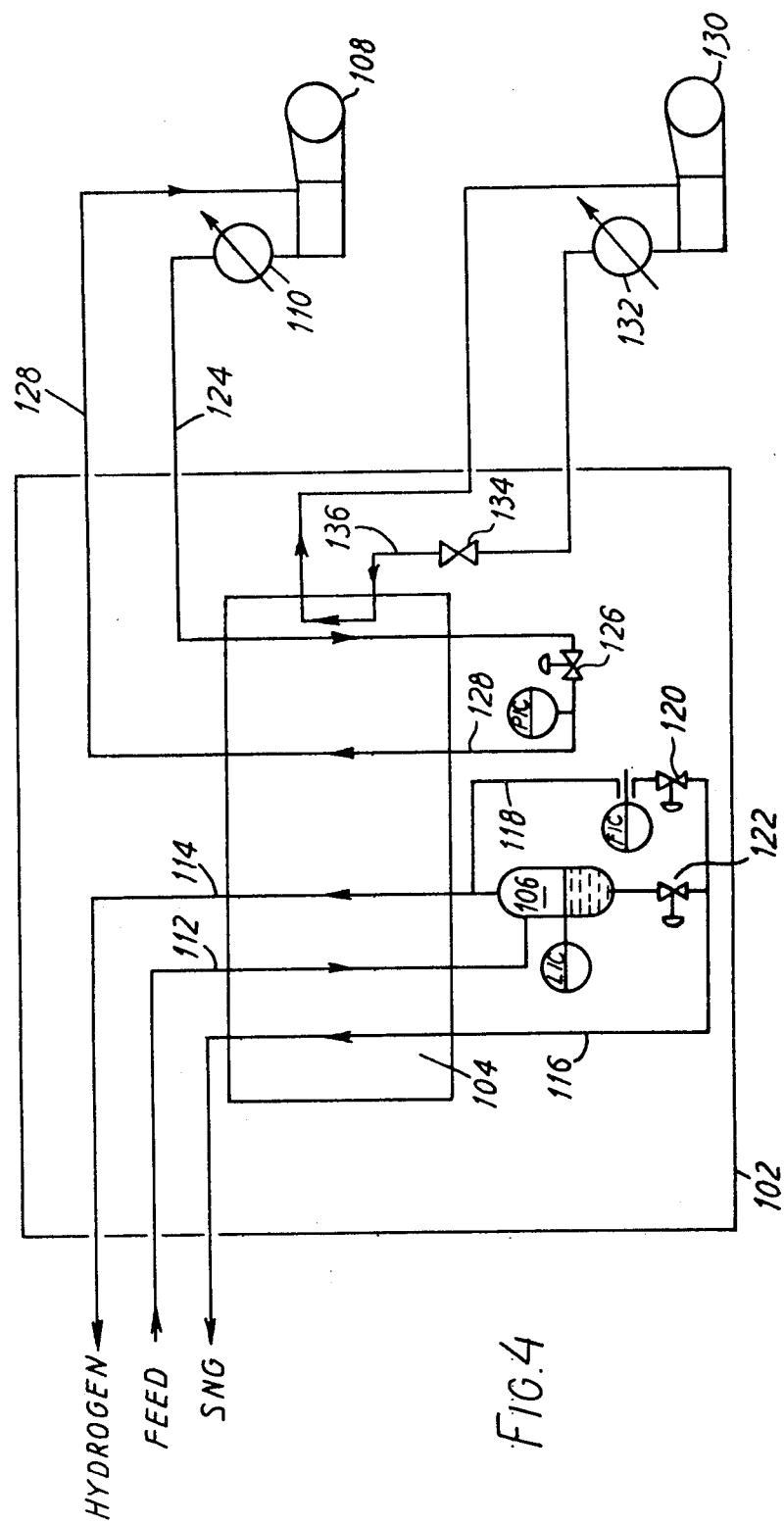
Figure 5:
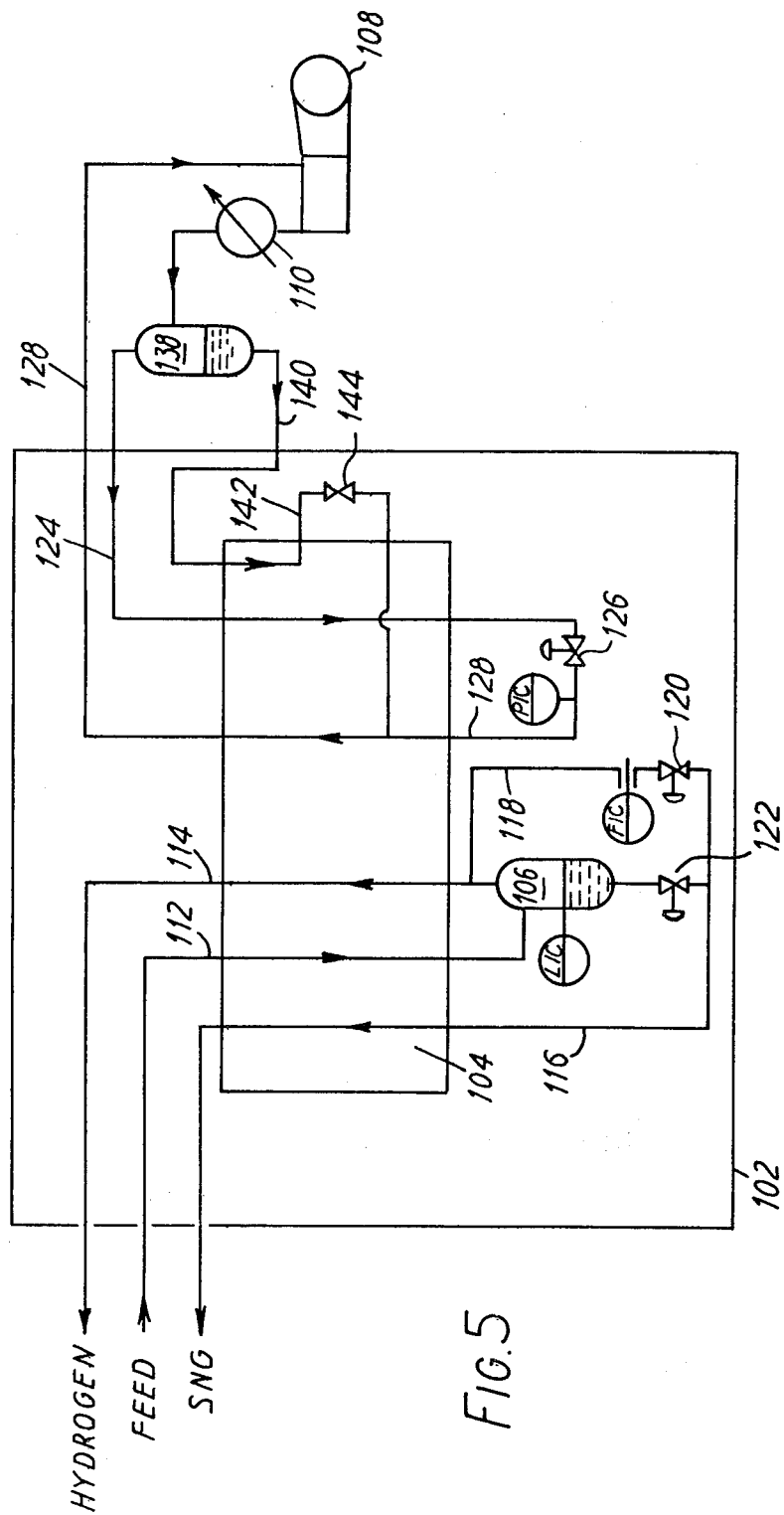

FIG. 1a shows a typical ideal relationship between warming and cooling curves without "crossover";
FIG. 1b shows a typical relationship with "crossover";
FIG. 1c shows a typical relationship where "crossover" is eliminated by "over refrigeration";
FIG. 2 shows a first embodiment of the invention;
FIG. 3 shows a second embodiment of the invention;
FIG. 4 shows a third embodiment of the invention;
FIG. 5 shows a forth embodiment of the invention.

A typical example is shown in FIG. 1a of the accompanying drawings in which the warming curve is shown as a broken line and the cooling curve is shown as a continuous line.

At a sufficiently low pressure of the returning evaporated liquid stream, generally termed "tail gas", it is often possible to fulfil the first of the above cited conditions, i.e. to obtain overall thermal balance between the feed and the returning products. However, in many cases this does not lead to the fulfilment of the other two conditions. Frequently, a "crossover" occurs, in that, over a certain temperature interval, generally in the lower temperature region, the warming curve comes to lie to the right of the cooling curve, thus rendering the process inoperable. (See FIG. 1b of the drawings.)

To correct this condition while still employing only the Joule-Thomson effect it becomes necessary to provide additional refrigeration at the cold end by decreasing the tail gas pressure and thus increasing the Joule-Thomson effect. This will satisfy the second requirement, eliminating the "crossover". However, as a result, the two curves will move apart at higher temperatures, leading to a large temperature difference at the warm end. Thus the third of the above conditions will not be satisfied; the plant will be "over-refrigerated" and hence inefficient. (See FIG. 1c of the drawings.)

It has now been found that this problem can be avoided by employing a heat pump which will provide refrigeration at the lower temperatures and remove refrigeration at the higher temperatures.

One case to which the invention may be applied is where for a part of the temperature range through which the feed gas mixture is being cooled, the sum of the enthalpies of the returning streams is less than the enthalpy of the feed gas mixture, whereby the warming curve lies to the right of the cooling curve for said part of the temperature range, i.e. the case illustrated in FIG. 1b. Another case to which the invention may be applied, however, is where for a part of the said temperature range, the sum of the enthalpies of the returning streams, while not being less than the enthalpy of the feed gas mixture, is not sufficiently greater for the process to be operable practically, e.g. because an uneconomically high or infinite heat exchange area would be required.

Thus, according to a first embodiment of the invention, a method of rendering operable a process for the separation of a gas mixture at superatmospheric pressure which comprises cooling the mixture from a first temperature $T_1$ to a sub-ambient temperature $T_2$ to partially condense it, separating thus formed condensate from uncondensed vapour, subjecting separated condensate to Joule-Thomson expansion and passing thus-expanded condensate and uncondensed vapour as returning streams in indirect counter-current heat exchange relationship with the feed gas mixture to cool the latter, and which process is inoperable by reason that for at least a part of the temperature range between $T_1$ and $T_2$ the sum of the enthalpies of the said returning streams is not sufficiently greater than the enthalpy of the feed gas mixture, comprises providing a closed heat pump cycle in which a multi-component gaseous medium is condensed at a superatmospheric pressure $P_1$ and over a first temperature range $\Delta T_A$ in indirect counter-current heat exchange relationship with said returning streams, the condensate is expanded by Joule-Thomson expansion to a lower pressure $P_2$, the expanded condensate is evaporated at pressure $P_2$ in indirect counter-current heat exchange relationship with said feed gas mixture and over a second temperature range $\Delta T_B$ which is lower than $\Delta T_A$, both $\Delta T_A$ and $\Delta T_B$ lying in the range defined by $T_1$ and $T_2$, and the evaporated expanded condensate is returned for recompression to pressure $P_1$ and recycle.

By means of this embodiment, additional refrigeration is provided towards the cold end of the process and automatically removed towards the warm end, and by appropriate choice of the temperature ranges $\Delta T_A$ and $\Delta T_B$ and of the amount of refrigeration provided in the temperature range $\Delta T_B$ and removed in the temperature range $\Delta T_A$, it is possible to eliminate any "cross-over" that would otherwise occur at the lower temperatures, or resolve any difficulties due to the warming and cooling curves approaching each other too closely at such lower temperatures, without widening the gap between the warming and cooling curves at the higher temperatures.

The methods for determining the shapes of warming and cooling curves for cryogenic operations of the kind described are well known by those skilled in the art and from this knowledge the desired values for the temperature ranges $\Delta T_A$ and $\Delta T_B$ for resolving any difficulties resulting from the warming and cooling curves approaching each other too closely, or "crossing-over" at the lower temperatures, can be determined.

The composition of the multi-component gaseous mixture employed as the heat pump medium and the values for pressures $P_1$ and $P_2$ are then chosen such that at $P_1$ the medium condenses in the range $\Delta T_A$ and at $P_2$ it evaporates in the range $\Delta T_B$. In practice, the composition will usually be selected on a trial and error basis but as a general rule it may be said that in the most widely applicable area of the invention, namely for processes for the separation of hydrogen rich gas from a feed gas stream containing hydrogen, the heat pump medium will usually comprise a mixture of light hydrocarbons (i.e. hydrocarbons containing 1 to 4 carbon atoms) and a minor proportion of nitrogen.

The amount of refrigeration provided and removed by the heat pump medium in the range $\Delta T_B$ and $\Delta T_A$, respectively, may be controlled by adjustment of the volume of heat pump medium circulating and/or the rate of circulation of the medium.

In general it will be preferred to operate the partial condensation process in heat balance without the heat pump, and thus the heat pump must also be balanced; i.e. so that the heat removed in the lower temperature range $\Delta T_B$ is equal to that introduced in the higher temperature range $\Delta T_A$. However, if desired the heat pump may be designed and operated so that the heat removed exceeds the heat introduced, or vice versa, to balance an otherwise unbalanced process. In particular, the heat pump may be used to provide additional refrigeration.

The process of the invention is particularly appropriate for those separation processes in which both $\Delta T_A$ and $\Delta T_B$ are below ambient temperature since then the heat equivalent of the net mechanical work consumed by the heat pump cycle may conveniently be rejected to a heat sink at ambient temperature, e.g. in a cold water cooler.

Additional cooling of the compressed heat pump medium at the pressure $P_1$ and/or superheating of the evaporated heat pump medium at the pressure $P_2$ may be required to achieve condensation and/or evaporation of the heat pump medium within the desired temperature ranges.

The cooling of the feed gas mixture by the returning vapour and expanded condensate streams may be effected in a single heat exchanger or two or more exchangers which may be in series and condensate formed in any heat exchanger may be removed, if desired, before the gas mixture is passed to a subsequent exchanger.

The process is particularly but not exclusively applicable to the separation of hydrogen-rich gas streams from gas mixtures containing hydrogen, especially those evolved in the gasification of coal or other solid hydrocarbon fuel and hydrogen-containing gas streams produced in the course of oil refining and petrochemical processes. The problem of "cross-over" tends to be particularly acute in the case of hydrogen-containing gas streams containing hydrocarbons and less than 65 mole % hydrogen, e.g. from 35 to 65 mole %.

The process overcomes the problem of avoiding "cross-over" at low temperatures without causing an undesirable widening of the gap between the warming and cooling curves at higher temperatures, and is more energy efficient than the alternative of reducing the pressure to which the condensate from the partial condensation is expanded and thereafter recompressing the evaporated condensate where it is desired to recover the tail gas at a higher pressure.

This embodiment is now described in greater detail with reference to one example thereof and with the aid of the flow sheet illustrated in FIG. 2 of the accompanying drawings and wherein the flows of the feed gas mixture and the products separated therefrom by partial condensation are indicated in full lines and the heat pump cycle is represented by a broken line. In the Figure, the numerals 1, 2, 3 and 4 denote heat exchangers, 5 is a liquid-vapour separator, 6 is a compressor, and 7 and 8 are expansion valves.

The feed gas mixture enters at superatmospheric pressure and ambient temperature through line 11, is cooled and partially condensed in exchangers 1 and 2, and liquid and vapour are separated in the vessel 5. For the purposes of illustrating this embodiment, it is assumed that it is desired to recover the vapour at a pressure close to that of the feed gas mixture and to recover the condensate at as high a pressure as possible commensurate with achieving overall heat balance. The vapour is therefore returned through both exchangers in line 12 without a significant drop in pressure. The condensate is expanded in valve 7 to the maximum pressure required for the overall heat balance of the process and is then returned in line 14 through exchangers 2 and 1, in which it is evaporated and warmed to near ambient temperature and recovered as tail gas.

If the resulting cooling and warming curves exhibit a cross-over as shown in FIG. 1b, the installation as so far described is not operable under these conditions and to render the plant operable it would be necessary, for example, to expand the condensate to a much lower pressure. However, if this were done, the warming and cooling curves would move far apart at the higher temperatures, e.g. as indicated in FIG. 1c, and the power required to recompress the tail gas would be excessive.

Instead, and in accordance with the invention, a much smaller compressor 6 is installed, which compresses a multi-component gaseous heat pump medium to a first pressure $P_1$. The heat of compression is rejected to cooling water in exchanger 4, and the compressed heat pump medium is passed in line 16 to enter the warm end of exchanger 2 wherein it is condensed over a first temperature range $\Delta T_A$ (and if desired sub-cooled) in counter-current heat exchanger relationship with the returning vapour and expanded condensate streams in lines 12 and 14. The condensed medium is withdrawn through line 17 from an intermediate point along heat exchanger 2 and the condensate is then expanded to a lower pressure $P_2$ in valve 8 and thereafter passed back through line 18 to enter the cold end of exchanger 2 wherein it is evaporated over a second temperature range $\Delta T_B$ (which is lower than $\Delta T_A$) in indirect counter-current heat exchange relationship with the feed gas mixture flowing in line 11 and also superheated. The heat pump medium in line 18 passes back through the entire length of heat exchanger 2 and is recovered from the warm end in line 19 whence it is returned to the compressor 6 through line 20. It will be understood that the condensing heat pump medium in line 16 flows in heat exchanger 2 co-currently with the feed gas mixture in line 11 and that the evaporating heat pump medium in line 18 flows in heat exchanger 2 co-currently with the returning vapour and expanded condensate streams in lines 12 and 14, respectively.

For the heat pump medium to be at the appropriate temperature when it enters heat exchanger 2 it may be necessary to provide a precooling step upstream of heat exchanger 2. Similarly, for the evaporated heat pump medium recovered from the warm end of said heat exchanger to be at an appropriate temperature at the inlet to the compressor, it may be necessary to warm it. In the arrangement illustrated, such pre-cooling and warming is achieved in heat exchanger 3 where the compressed heat pump medium in line 15 is pre-cooled by the same medium returning at low pressure in line 19. It will be apparent to those skilled in the art that many modifications of the illustrated arrangement of heat exchangers are possible without departing from the invention. For example, heat exchanger 3 may be combined with heat exchanger 1 in the same vessel as a single multi-system unit. Also, heat exchanger 2 may be split into two exchangers in series whereby line 16 passes through one of the exchangers and line 18 passes through both.

By this means and by appropriate choice of the composition of the heat pump medium and the pressure to which it is compressed in compressor 6 and expanded in expansion valve 8, the cooling and warming curves can be brought to the desired relative position to make the plant operable and the power consumption is significantly less than would be the case if the tail gas itself were expanded to a lower pressure and recompressed.

In a second embodiment of the present invention, the expansion of the condensate is dispensed with and both refrigeration and energy requirements are provided from the heat pump itself, optionally supplemented by a separate refrigeration cycle.

Thus, according to this second embodiment, there is provided a method of separating a gas mixture under pressure by partial condensation and recovering a product stream derived from the condensate at a superatmospheric pressure not substantially below that at which the gas mixture is supplied, the method comprising cooling the gas mixture at superatmospheric pressure to sub-ambient temperature to partially condense it, separating condensate from uncondensed gas and without subjecting the condensate to any significant expansion warming the separated streams by indirect counter-current heat exchange with the feed gas mixture, the product stream being provided from the warmed condensate, and providing refrigeration and energy requirements of the separation by means of a heat pump alone or together with at least one separate refrigeration cycle and wherein in the heat pump a multi-component gaseous medium is compressed, the compressed medium is thereafter condensed in indirect counter-current heat exchange relationship with said separated streams, the condensed medium is then expanded and evaporated in indirect counter-current heat exchange relationship with said feed gas mixture and condensed medium at a temperature range which is lower than that in which the medium is condensed, and the evaporated medium is returned for recompression.

By "without subjecting the condensate to any significant expansion" we mean that the condensate is not subjected to an expansion such as to provide any significant cold for the process. However such expansion as may occur through employment of e.g. flow control valves is not excluded.

By stating that the temperature range over which the expanded heat pump medium evaporates is lower then that over which the same medium is condensed, we mean that the upper value of the first-mentioned temperature range is below the upper value of the second-mentioned temperature range and likewise for the lower values. Thus the first-mentioned temperature range may fall entirely below the second or the ranges may overlap.

It is generally desirable to sub-cool the condensed heat exchange medium in order to minimise or avoid flash when it is expanded. The sub-cooling is conveniently effected by heat exchange with the separated streams and its expanded self and can be carried out in the same heat exchanger as the condensation.

The method provides a substantial saving in energy compared with the alternatives of providing all the refrigeration and energy requirements of the process by expansion of the condensate or by a combination of expansion of the condensate and a heat pump as described in the aforementioned copending patent application. Moreover in that embodiment of the present invention in which no separate refrigeration cycle is employed, the machinery requirement, as compared with the process of the copending patent application, is reduced.

Where minor quantities of the uncondensed gas can be tolerated in the product obtained from the condensate, it has been found advantageous to inject a quantity of the uncondensed gas into the condensate prior to warming the latter in heat exchange with the incoming feed gas mixture. This has the effect of displacing the combined warming curve to the left in the lower temperature region and reduces the duty of the heat pump and the power consumed by it. While this benefit increases with increase in the amount injected, the injection counteracts the objective of the separation and therefore the amount injected will generally be relatively small. The optimum situation will depend upon the nature of the feed gas and the intended use of the separated condensate. By way of example, for the production of synthetic natural gas from hydrogen-containing gas streams such as those obtained from the gasification of solid hydrocarbon fuels or in the course of oil refining or petrochemical processes, the amount of uncondensed gas injected into the condensate typically will be about 2% to 3% by volume of the feed gas but may be as much as up to 8%.

(Injecting a minor quantity of the uncondensed gas into the expanded condensate prior to warming the latter in heat exchange with the incoming feed gas mixture in the process of the first-described embodiment of this invention will give a similar advantage in that process.)

In one aspect of the second embodiment of the invention, the heat pump is employed primarily or only to provide the energy for the separation and the refrigeration requirement is supplied by one or more separate refrigeration cycles. In this case, the heat pump will be substantially in balance; that is, so that there is no significant difference between the enthalpy $H_{CHP}$ of the compressed heat pump medium entering the warm end of the heat exchange system to be heat exchanged with the separated streams and the enthalpy $H_{EHP}$ of the expanded heat pump medium leaving said warm end of the heat exchange system after it has been evaporated by heat exchange with the feed gas mixture. The refrigeration requirements of the process are provided by any suitable refrigeration cycle or cycles.

In another aspect, the heat pump provides not only the work for the separation but also at least part of the refrigeration. In this embodiment, the heat pump is designed to be out of balance so that $H_{EHP}$ is greater than $H_{CHP}$ and there is net refrigeration. The "unbalancing" may be achieved in known manner, e.g. by increasing the proportion of high boiling components in the multi-component heat pump cycle medium and if necessary the pressure to which the medium is compressed and/or by increasing the pressure drop to which the medium is submitted during expansion.

In yet another aspect, the refrigeration may be provided by means of a vapour compression refrigeration cycle which employs as the cycle medium condensate obtained by partially condensing the compressed heat pump cycle medium prior to heat exchanging said compressed medium with the separated streams. To achieve this, the composition of the heat pump cycle medium will include at least one component which, after the medium has been compressed, can be condensed, e.g. by heat exchange with cooling water, prior to heat exchanging the compressed medium with the separated streams. The condensate is then separated from the uncondensed material prior to said heat exchange with the separated streams and employed in the refrigeration cycle, where it is first sub-cooled (usually) and then expanded and thereafter recombined with warming low pressure heat pump medium and evaporated in the warm section of the heat exchanger before returning to the suction side of the compressor.

Like the first, the second embodiment is particularly applicable to the separation of gas mixtures wherein the minimum pressure drop to which separated condensate would have to be submitted in order to provide the refrigeration for the process would be insufficient for operability of the process because for at least a part of the cooling range the combined warming curve would not fall sufficiently far to the left, and might even cross over and fall to the right of the cooling curve. Examples of such separation processes are those for the recovery of hydrogen-rich gases from hydrogen-containing gas streams such as those obtained by the gasification of coal or other solid hydrocarbon fuels or in the course of oil refining and petrochemical processes, especially hydrogen-containing streams which comprise mixtures of hydrogen with hydrocarbons containing not more than 80 mole % hydrogen, e.g. from 20 to 80 mole%, more particularly 35 to 70 mol%. The process of the invention is particularly suitable for the production of synthetic natural gas (SNG) from such streams.

The methods for determining the shapes of the warming curve and the combined cooling curve referred to above are well known and from this knowledge can be determined the nature of the heat pump cycle required to provide the work of separtion.

For example, one convenient way of determining the parameters of the required heat pump cycle is to plot against temperature T the vertical gap $\Delta H$ between the cooling curve and the combined warming curve. The desired heat pump cycle is that in which the curve which is obtained by likewise plotting against temperature the enthalpy difference between the heat pump medium in the compressed form and the heat pump medium in the expanded form, corresponds as closely as possible to the aforementioned curve obtained for $\Delta H$ against T and lies above it at all points. The shape of the curve obtained for the heat pump cycle will be determined by the composition of the heat pump medium and the pressures to which it is compressed and expanded. The nature of the composition and the values for these pressures can be determined by simple experiment. In practice, the nature of the composition is selected on a trial and error basis but as a general rule it may be said that in the most widely applicable area of the invention, namely for processes for separating a hydrogen-rich gas from a feed gas stream containing hydrogen, the heat pump medium will usually comprise a mixture of light hydrocarbons (i.e. hydrocarbons containing 1 to 4 carbon atoms) and a minor proportion of nitrogen.

In many cases, it will be found that the hydrocarbon portion of the heat pump medium can be synthesised from the separated condensate and that the medium can be formed by adding one or more compounds, especially nitrogen, to a material having the same composition as the condensate or which has been derived from the condensate e.g. by distillation.

The amount of refrigeration provided and removed by the heat pump may be controlled by adjustment of the rate of circulation of the heat pump medium.

The second embodiment of the invention is now described in more detail with reference to preferred examples thereof and with the aid of the accompanying drawings in which FIG. 3 is a flow sheet of an arrangement according to the invention in which an unbalanced heat pump provides all the refrigeration and the energy requirements for the separation FIG. 4 is a flow sheet of a similar arrangement but wherein at least some of the refrigeration is provided by a separate refrigeration cycle, and FIG. 5 is a flow sheet of an arrangement similar to that of FIG. 4 but wherein the refrigeration is provided by a vapour compression refrigeration cycle wherein the refrigerant is divided from the medium employed in the heat pump cycle.

Referring to FIG. 3, 102 is a cold box, 104 is a heat exchanger, 106 is a liquid/vapour separator, 108 is a compressor and 110 is a compressor after-cooler.

The feed gas mixture enters the cold box at superatmospheric pressure and ambient temperature through line 112, is cooled and partially condensed in heat exchager 104 and the resulting liquid and vapour are separated in liquid/vapour separator 106, the uncondensed portion returning through heat exchanger 104 in line 114 and the condensate returning through line 116 in which it is warmed and evaporated by heat exchange in exchanger 104.

Prior to entering the cold end of the heat exchanger 104, a bleed stream 118 is withdrawn from the uncondensed gas and injected into the condensate in line 116. The rate of flow in line 118 is controlled by flow control valve 120 and that of condensate from the separator is controlled by level control valve 122.

The refrigeration and energy requirements of the process are provided by a heat pump in which a multicomponent heat pump medium of appropriate composition is compressed to a first pressure in compressor 108 and, after the heat of compression has been rejected to cooling water in cooler 110, is passed via line 124 to enter the warm end of heat exchanger 104 wherein it is cooled and condensed over a first temperature range in heat exchange with the streams in line 114, 116 and 128. The condensed medium is recovered from the cold end of the exchanger, expanded to a lower pressure through expansion valve 126 and thereafter returned via line 128 to enter the cold end of the exchanger wherein it is evaporated in heat exchange with the streams in lines 112 and 124 and over a second temperature range which is lower than the temperature range at which it was condensed. The heat pump provides refrigeration in the colder region of the heat exchanger and removes refrigeration from the warmer region, and can thus be arranged to ensure that the warming curve is sufficiently far to the left of the cooling curve for operability over the whole temperature range of the heat exchange system without unduly widening the gap at the higher temperatures of the system.

In order to provide the refrigeration requirements of the process, the composition of the heat pump medium and the pressure drop to which it is submitted on expansion through valve 126 are chosen such that the heat pump is unbalanced and produces the desired amount of net refrigeration.

In the alternative arrangement illustrated in FIG. 4, the features common with those of the arrangement of FIG. 3 have the same reference numerals, but there is a difference in that the composition of the heat pump medium and the pressure drop across expansion valve 126 are chosen such that the heat pump is not intentionally out of balance. In this arrangement, the refrigeration requirement for the process is satisfied by a separate refrigeration cycle which, in the embodiment illustrated, is a conventional vapour compression refrigeration cycle in which refrigerant is compressed in compressor 130, and, after the heat of compression has been removed in compressor after-cooler 132, expanded through expansion valve 134 and thereafter passed in line 136 through an additional passageway in heat exchanger 104, where it gives up its cold, and returned to the inlet of the compressor.

An alternative to the arrangement illustrated in FIG. 4 is illustrated in FIG. 5 wherein the features common with those of the arrangement of FIG. 4 are again given the same reference numerals. In this arrangement, refrigeration for the process is provided by a vapour compression refrigeration cycle the refrigerant for which is provided by arranging for the heat pump medium to have a composition such that it is partially condensed on cooling in the compressor after-cooler 110. The mixture of vapour and liquid so obtained is then passed to vapour/liquid separator 138 and the uncondensed vapour is removed in line 124 to form the compressed heat pump medium which is condensed in heat exchanger 104 as in the arrangement of FIG. 4. The condensate, which is recovered in line 140, forms the refrigerant for the vapour compression refrigeration cycle. It is sub-cooled in an extra passageway in heat exchanger 104, removed from the heat exchanger at an intermediate position through line 142, expanded through expansion valve 144 and thereafter injected into line 128, which carries the evaporating low pressure heat pump medium through the heat exchanger 104, at another intermediate point in the heat exchanger, whereby it is evaporated in the heat exchanger to satisfy the refrigeration requirements of the process.

Modifications of the arrangements illustrated in FIGS. 3 to 5 will be apparent to those skilled in the art. For example, heat exchanger 104 may be replaced by two or more heat exchangers which may be in parallel and/or in series. Either or both of compressors 108 and 130 may be multi-stage compressors. The single stage partial condensation of the feed gas mixture entering in line 112 may be replaced by a multi-stage process e.g. with separation of condensate after each stage. The partial condensation of the compressed medium recovered from the compressor 108 in the arrangement illustrated in FIG. 5 may be effected in part in the compressor after-cooler 110 and in part in at least one further heat exchanger or alternatively entirely in a further heat exchanger or exchangers. The refrigeration requirements may be provided in part by the heat pump and in part by a separate refrigeration cycle and/or by a refrigeration cycle in which the refrigerant is obtained by partial condensation of the heat pump medium prior to heat exchanging same with the returning streams in the heat exchanger. Moreover, the process can be achieved, although less efficiently, without the injection of the bleed stream 118 into the condensate line 116.

The invention is now illustrated by the following Examples in which Example 1 illustrates the first embodiment and Examples 2 to 4 illustrate the second.

EXAMPLE 1

A feed gas mixture in line 11, (FIG. 2) available at 52 bar and 40° C., has the following composition:

|  | M% |
|---|---|
| $H_2$ | 57.9 |
| CO | 1.0 |
| $CH_4$ | 25.9 |
| $C_2H_6$ | 14.4 |
| $C_2H_4$ | 0.3 |
| $C_3H_6$ | 0.4 |

| | M% |
|---|---|
| C₃H₈ | 0.1 |
| | 100.0 |

The flow rate is 14400 kg.mol/hr.

It is desired to recover a hydrogen-rich product containing 95% H$_2$ and at a delivery pressure of 51 bar. The hydrogen recovery is to be 95%. The tail gas is required to be delivered at 52 bar.

For a process relying for refrigeration solely on Joule-Thomson expansion of the condensate in line 13, it is calculated that the maximum tail gas pressure to secure overall heat balance is 15 bar. At higher tail gas pressures the refrigeration is inadequate. At a tail gas pressure of 15 bar, the plant is in overall heat balance but the cooling and warming curves cross over as illustrated in FIG. 1b. Below 215° K. the cooling curve lies to the left of the warming curve, crossing back again near the lowest temperature of the process at around 118° K.

A heat pump cycle is provided as illustrated in the drawing with a heat pump medium having the following composition:

| | mole % |
|---|---|
| N$_2$ | 9 |
| CH$_4$ | 60 |
| C$_2$H$_4$ | 16 |
| C$_2$H$_6$ | 15 |
| | 100 | and a flow rate of 1480 kg.mol/hr. The heat pump compressor operates between 1.5 bar at which the medium evaporates in the range 98°–166° K., and 25 bar (P$_1$) at which the medium condenses in the range 221°–165° K. The heat pump medium enters exchanger 2 at its dew-point of 221° K., and leaves at the intermediate point, subcooled to 125° K.

The temperatures of the streams at various points in the arrangement are as follows.

| | Temperature (°K.) |
|---|---|
| Feed stream in line 11: | |
| entering heat exchanger 1 | 313 |
| leaving heat exchanger 1 | 221 |
| leaving heat exchanger 2 | 118 |
| Uncondensed gas in line 12: | |
| entering heat exchanger 2 | 118 |
| leaving heat exchanger 2 | 217 |
| leaving heat exchanger 1 | 310 |
| Expanded condensate in line 14: | |
| entering heat exchanger 2 | 120 |
| leaving heat exchanger 2 | 217 |
| leaving heat exchanger 1 | 310 |
| Heat Pump Medium: | |
| H.P. in line 15 entering heat exchanger 3 | 308 |
| H.P. in line 16 entering heat exchanger 2 | 221 |
| H.P. in line 17 leaving heat exchanger 2 | 125 |
| L.P. in line 18 re-entering heat exchanger 2 | 112 |
| L.P. in line 19 leaving heat exchanger 2 | 187 |
| L.P. in line 20 leaving heat exchanger 3 | 303 |

The power consumed by the heat pump compressor is 4320 kw and the power consumed by the tail gas compressor in compressing the tail gas from 15 to 52 bar is 8300 kw, giving a totl power consumption for the process of 12620 kw.

To obtain an operable plant without the heat pump, the condensate would have to be expanded to 2.5 bar. This would lead to a power consumption of 19600 kw for compressing the tail gas. Even if a part of the tail gas only is expanded to 2.5 bar and the rest to an intermediate pressure, the power consumption could be reduced to 16800 kw, but this is still significantly higher than that required using the heat pump.

In the above Example, P$_1$, the pressure at which the heat pump medium is condensed, is 25 bar and pressure P$_2$, the pressure at which the medium is evaporated, is 1.5 bar. $\Delta T_A$, the temperature range at which the heat pump medium condenses in indirect counter-current heat exchange relationship with the returning streams, is 221°–165° K. $\Delta T_A$, the temperature range at which the same medium evaporates in indirect counter-current heat exchange relationship with the feed gas mixture, is 112° K. (the temperature at which the medium re-enters heat exchanger 2 after expansion to pressure P$_2$) −166° K.

In each of the following Examples, which illustrate the second embodiment of the invention, a feed stream having the composition and flow rate given below is separated into a synthetic natural gas (SNG) stream and a residual hydrogen stream, each having the composition and flow rate indicated.

| | Feed entering in line 112 mol % | Hydrogen recovered from plant in line 114 mol % | SNG recovered from plant in line 116 mol % |
|---|---|---|---|
| COMPOSITION | | | |
| H$_2$ | 56.03 | 95.08 | 10.00 |
| N$_2$ | 0.06 | 0.06 | 0.06 |
| CO | 0.84 | 0.67 | 1.04 |
| Ar | 0.09 | 0.05 | 0.14 |
| CH$_4$ | 34.94 | 4.14 | 71.25 |
| C$_2$H$_4$ | 0.12 | — | 0.26 |
| C$_2$H$_6$ | 7.92 | — | 17.25 |
| FLOW RATE | | | |
| kmol/hr | 10544 | 5704.4 | 4839.6 |

The flow in line 118 equals about 3% of the flow rate of the Feed.

EXAMPLE 2

Using the arrangement illustrated in FIG. 3, the feed gas mixture in line 112 enters the cold box 102 at 58.6 bar absolute and is cooled in heat exchanger 104 from 303 K. to 115 K. The condensate recovered from vapour/liquid separator 106 under level control, and containing uncondensed gas injected through line 118, is evaporated in the heat exchanger and recovered at 57.6 bar absolute and 300 K. The vapour in line 114 is also recovered from the heat exchanger at 57.6 bar absolute and 300 K.

To provide the energy and refrigeration requirements of the process, a heat pump medium having the following molar composition: nitrogen 12%, methane 44%, ethylene 39%, isobutane 5%, is circulated at a rate of 2333 kmol/hr through compressor 108, compressor after-cooler 110, line 124, expansion valve 126 and line 128. After leaving the compressor 108 at 50 bar, the heat of compression is removed in after-cooler 110 and the medium enters the warm end of heat exchanger 104 in line 124 wherein it is cooled, condensed and sub-cooled to 115 K. It is then expanded to 2.0 bar absolute and 108.5 K. in valve 126 and returned to the heat exchanger in line 128 wherein it is evaporated and warmed to 300 K. before being returned to the suction side of the compressor at a pressure of 1.8 bar absolute.

The power consumption of the compressor is 8010 kW.

By way of comparison, if the same feed gas is separated into the same products but with the energy and refrigeration requirements of the process being supplied by expansion of the condensate in line 116 instead of using a heat pump, it is necessary to expand the condensate to 3 bar absolute and the power required to recompress the SNG to the same recovery pressure of 57.6 bar absolute is 14500 kW. The process of the invention therefore provides an energy saving of 45%.

Example 3

The pressures and temperatures of the incoming feed gas mixture, the recovered SNG and the recovered hydrogen stream, and the temperature to which the feed gas mixture is cooled in the heat exchanger, are the same as in Example 2. In this Example, however, the arrangement of FIG. 4 is employed; that is, the heat pump cycle is arranged to be more nearly in balance than in the arrangement of FIG. 3 and a significant part of the refrigeration requirements are provided by a separate refrigeration cycle.

To achieve this, the composition of the heat pump medium is adjusted to 12% nitrogen, 41% methane, 42% ethylene and 5% isobutane (molar) and is circulated at a rate of 3045 kmol/hr. It is compressed to 30.0 bar absolute in compressor 108 and, after removal of the heat of compression, is condensed in heat exchanger 104 and sub-cooled to 115 K. The condensate is then expanded to 3.0 bar absolute and 110 K. in expansion valve 126 and returned to the heat exchanger where it is evaporated and warmed to 300 K before being returned to the suction side of the compressor.

To provide the refrigeration requirements, refrigerant R22 is supplied in line 136 to heat exchanger 104 at a pressure of 2.16 bar absolute, a temperature of 250 K. and a flow rate of 106 kmol/hr.

The power consumptions of the heat pump compressor and refrigerator compressor are 7477 and 161 kW, respectively, a total of 7638 kW. This arrangement is thus even more economical in power than that of Example 2.

By way of comparison, if the process is repeated but with the refrigeration requirements provided instead by expansion of the condensate recovered from the vapour/liquid separator 106 instead of by the separate refrigeration cycle, it would be necessary to expand the condensate to 19.5 bar absolute. In order to adjust for the consequential change in distribution of heat and cold requirements in the heat exchanger 104, it is necessary to adjust the composition and conditions of the heat pump cycle. The altered conditions are satisfied by a heat pump medium composition of 15% nitrogen, 65% methane and 20% ethylene (molar), a flow rate of 1061.4 kmol/hr and pressures of 20 bar and 1.5 bar, requiring a heat pump compressor power consumption of 2830 kW. This power consumption is reduced because a substantial part of the energy of separation is also supplied by the expansion of the condensate.

The power requirements for re-compressing the expanded condensate from 19.5 bar to 57.6 bar absolute are 5440 kW, making a total of 8270 kW, an increase of about 8%.

If Example 2 or Example 3 is repeated but without the injection of the bleed stream in line 118 into the condensate in line 116, a lower but still significant power saving can be obtained by means of the processes described therein, compared with the conventional arrangement whereby the refrigeration and energy requirements are provided by expanding the condensate which thereafter has to be recompressed.

Example 4

The pressure and temperature of the incoming feed gas mixture and the temperature to which the feed gas mixture is cooled in the heat exchanger 104 are the same as in Example 2. In this Example, however, the arrangement of FIG. 5 is employed.

A stream having a composition of 12% nitrogen, 14% methane, 30% ethylene and 17% isobutane and circulating at the rate of 3600 kmol/hr and which has been compressed to 40 bar absolute in compressor 108 is cooled in after-cooler 110 to 303 K. and thereby partially condensed to produce 152 kmol/hr of liquid. This liquid is separated in separator 138 and recovered in line 140, passed to heat exchanger 104 where it is sub-cooled and recovered therefrom at an intermediate point in line 142 at 250 K. It is then expanded to 3.0 bar absolute and 230 K. in expansion valve 144 and returned to the exchanger at another intermediate point to provide refrigeration for the process.

The uncondensed vapour recovered from separator 138 is condensed and sub-cooled in line 124 in heat exchanger 104 to 115 K., expanded to 3.0 bar absolute and 110.6 K. and returned in line 128 to the heat exchanger wherein it is warmed to 235 K., combined with the expanded fluid from the refrigeration circuit and the mixture recovered as a gas from the warm end of the exchanger at 295 K. The hydrogen and SNG streams are also both recovered at 295 K.

The power consumption of compressor 108 in this case is 9778 kW.

In all the above Examples, it is possible to replace the ethylene in the heat pump medium by ethane.

We claim:

1. In a process for the separation of a gas mixture at a superatmospheric pressure which comprises cooling the mixture from a first temperature $T_1$ to a sub-ambient temperature $T_2$ to partially condense it, separating the thus-formed condensate from uncondensed vapour, subjecting the separated condensate to Joule-Thomson expansion and passing the thus-expanded condensate and uncondensed vapour as returning streams in indirect counter-current heat exchange relationship with the feed gas mixture to cool the latter, and which process would be rendered inoperable but for the below-named improvement by reason that for at least a part of the temperature range between $T_1$ and $T_2$, the sum of the enthalpies of the returning streams is not sufficiently greater than the enthalpy of the feed gas mixture; the improvement comprising providing a closed heat pump cycle in which a multi-component gaseous medium is condensed in a heat-emitting line at a superatmosphere pressure $P_1$ and over a first temperature range $\Delta T_A$ in indirect counter-current heat exchange relationship with said returning streams, the resulting condensate in said heat pump cycle is expanded by Joule-Thomson expansion to a lower pressure $P_2$, the expanded condensate is evaporated in a heat-absorbing line at the pressure $P_2$ in indirect counter-current heat exchange relationship with said feed gas mixture and over a second temperature range $\Delta T_B$ which is lower than the range $\Delta T_A$, both said ranges $\Delta T_A$ and $\Delta T_B$ lying within the range defined by the temperatures $T_1$ and $T_2$, and the evaporated expanded condensate is returned for recompression to the pressure $P_1$ and is recycled, such that said multi-component gaseous medium in the heat pump cycle absorbs heat from the feed gas mixture in the lower range $\Delta T_B$ and transfers heat to said separated product streams in the higher temperature range $\Delta T_B$ sufficient to provide that at all points within the range defined by the temperatures $T_1$ and $T_2$ the temperature of the feed gas mixture is greater than the temperature of the returning separated product streams and the temperature difference between the feed gas mixture and the returning separated product streams is small.

2. A process as claimed in claim 1 in which the ranges $\Delta T_A$ and $\Delta T_B$ are both below ambient temperature.

3. A process as claimed in claim 1 in which the heat given up by the condensation of the heat pump medium at the pressure $P_1$ is substantially equal to the heat absorbed by evaporation of the heat pump medium at $P_2$.

4. A process as claimed in claim 1 in which the gas mixture contains hydrogen and a hydrogen-rich stream is separated therefrom.

5. A process as claimed in claim 4 in which the gas mixture is obtained by the gasification of coal or other solid hydrocarbon fuel.

6. A process as claimed in claim 4 in which the gas mixture is provided from a gas stream produced in the course of oil refining or of a petrochemical process.

7. A process as claimed in claim 4 in which the gas mixture contains less than 65 mole % hydrogen.

8. A process as claimed in claim 4 in which the multi-component heat pump medium comprises a mixture of nitrogen and light hydrocarbons in which the nitrogen is present in a minor amount.

9. A process as claimed in claim 8 in which the multi-component heat pump medium comprises nitrogen, methane, ethylene and ethane.

10. A process as claimed in claim 1 in which the duty of the heat pump is reduced by injecting a portion of the uncondensed vapour into the expanded condensate prior to passing the latter in indirect counter-current heat exchange relationship with the feed gas mixture.

11. A method of separating a gas mixture under pressure by partial condensation and recovering a product stream from the condensate at a superatmospheric pressure not substantially below that at which the gas mixture is supplied, the method comprising
cooling the gas mixture at superatmospheric pressure to sub-ambient temperature to partially condense it,
separating condensate from uncondensed gas and without subjecting the condensate to any significant expansion warming the separate streams by indirect counter-current heat exchange with the feed gas mixture the product stream being provided from said warmed condensate, and
providing refrigeration and energy requirements of the separation by means of a heat pump along or together with at least one separate refrigeration cycle and wherein in the heat pump a multi-component gaseous medium is compressed, the compressed medium is thereafter condensed in indirect counter-current heat exchange relationship with said separated streams, the condensed medium is then expanded and evaporated in indirect counter-current heat exchange relationship with said feed gas mixture and condensed medium at a temperature range which is lower than that in which the medium is condensed, and the evaporated medium is returned for recompression, such that said multi-component gaseous medium in the heat pump absorbs heat from the feed gas mixture in the lower temperature range and transfers heat to said separated product streams in the higher temperature range sufficient to provide that at all points wherein said indirect counter-current heat exchange between said separated streams and said feed gas mixture takes place the temperature of the feed gas mixture is greater than the temperature of the returning separated product streams and the temperature difference between the feed gas mixture and the returning separated product streams is small.

12. A process as claimed in claim 11 wherein the refrigeration is supplied by arranging for the heat pump to provide net refrigeration.

13. A process as claimed in claim 11 wherein the refrigeration is supplied by means of a vapour compression refrigeration cycle wherein the cycle medium comprises condensate obtained by partially condensing the compressed heat pump medium prior to passing said compressed medium in indirect heat exchange relationship with said separated streams.

14. A process as claimed in claim 11 in which the duty of the heat pump is reduced by injecting a portion of the uncondensed gas into the separated condensate prior to warming the latter by indirect heat exchange with the incoming feed gas mixture.

15. A process as claimed in claim 11 in which the condensed heat pump medium is sub-cooled prior to expansion.

16. A process as claimed in claim 11 in which the gas mixture comprises a mixture of hydrocarbons and hydrogen and contains 20 to 80 mol % hydrogen.

17. A process as claimed in claim 11 for the production of synthetic natural gas from a hydrogen-containing gas stream obtained by the gasification of a solid fuel or in the course of oil refining or a petrochemical process.

18. A method of separating a gas mixture under pressure by partial condensation and recovering a product stream from the condensate, the method comprising cooling the gas mixture at superatmospheric pressure to sub-ambient temperature to partially condense it; separating condensate from uncondensed gas and with or without subjecting the condensate to any significant expansion warming the separated streams by indirect counter-current heat exchange with the feed gas mixture, the product stream being provided from said warmed condensate; providing a heat pump wherein a multi-component gaseous medium is compressed, the compressed medium is thereafter condensed in indirect counter-current heat exchange relationship with said separated streams, the condensed medium is then expanded and evaporated in indirect counter-current heat exchange relationship with said feed gas mixture and condensed medium at a temperature range which is lower than that in which the medium is condensed, and the evaporated medium is returned for recompression, such that said multi-component gaseous medium in the heat pump absorbs heat from said feed gas mixture in the lower temperature range and transfers heat to said separated product streams in the higher temperature range sufficient to provide that at all points within the region of said counter-current heat exchange the temperature of the feed gas mixture is greater than the temperature of the returning separated product streams and the temperature difference between the feed gas mixture and the returning separated product streams is small; and providing the refrigeration requirements of the separation either by one or another of expansion of the condensate formed by said partial condensation of said gas mixture, said heat pump alone, said heat pump together with at least one refrigeration cycle, and the combination of expansion of the condensate and a heat pump.

* * * * *